United States Patent [19]

Bunnell

[11] Patent Number: 5,084,568
[45] Date of Patent: Jan. 28, 1992

[54] PROCESS FOR PREPARING ACID HALIDES

[75] Inventor: Charles A. Bunnell, Lafayette, Ind.

[73] Assignee: Eli Lilly and Company, Indianapolis, Ind.

[21] Appl. No.: 628,242

[22] Filed: Dec. 17, 1990

Related U.S. Application Data

[62] Division of Ser. No. 305,145, Feb. 2, 1989, Pat. No. 5,013,854.

[51] Int. Cl.$^5$ .............. C07D 223/04; C07D 333/06; C07D 307/38
[52] U.S. Cl. ............................ 540/487; 544/229; 544/335; 546/275; 546/281; 546/335; 548/110; 548/406; 548/465; 548/495; 549/4; 549/214; 556/407; 556/408; 556/418; 556/422
[58] Field of Search ............... 549/214; 556/407, 408, 556/418, 422; 548/110, 406, 465, 495; 546/275, 281, 335; 544/229, 335; 540/487

[56] References Cited

U.S. PATENT DOCUMENTS

| | | | |
|---|---|---|---|
| 2,573,302 | 10/1951 | Bidaud et al. | 260/448.2 |
| 3,951,982 | 4/1976 | Goel | 260/268 |
| 3,971,778 | 7/1976 | Cook et al. | 260/243 |
| 4,017,515 | 4/1977 | Cook et al. | 260/332.3 |
| 4,072,710 | 2/1978 | Coll | 260/544 |
| 4,379,766 | 4/1983 | Mack et al. | 260/413 |
| 4,400,509 | 8/1983 | Bruynes et al. | 544/315 |

FOREIGN PATENT DOCUMENTS

| | | |
|---|---|---|
| 488531 | 12/1952 | Canada . |
| 2550039 | 5/1976 | Fed. Rep. of Germany . |
| 2639742 | 3/1977 | Fed. Rep. of Germany . |
| 1520297 | 8/1978 | United Kingdom . |
| 1534320 | 11/1978 | United Kingdom . |

OTHER PUBLICATIONS

Anderson, H. H., "Monoethylgermanium and Alkylsilicon Esters. Dimethylgermanium Diacetate", *Journal of the American Chemical Society*, 74, 2371–2372 (1952).

Chaudhary, S. K. et al., "4-Dimethylaminopyridine: An Efficient and Selective Catalyst for the Silylation of Alcohols", *Tetrahedron Letters*, 99, (1979).

G. Lancaster et al., *Clinica Chimica Acta*, 48, 279–285 (1973).

*Primary Examiner*—Alan L. Rotman
*Assistant Examiner*—A. A. Owens
*Attorney, Agent, or Firm*—James J. Sales; Leroy Whitaker

[57] ABSTRACT

An improved process for preparing trialkylsilyl ester and acid halide derivatives of carboxylic acids is provided along with novel trialkylsilyl ester intermediates of 2-(2-furyl)-2-methoximinoacetic acid.

3 Claims, No Drawings

5,084,568

PROCESS FOR PREPARING ACID HALIDES

This application is a division of application Ser. No. 07/305,145, filed Feb. 2, 1989 now U.S. Pat. No. 5,013,854.

BACKGROUND OF THE INVENTION

This invention relates to a process for the preparation of carboxylic acid halides. In particular, it relates to a process for preparing silyl esters of carboxylic acids which are directly convertible to acid halides.

There are many methods available for preparing acid halides, most typically from the free-carboxylic acid itself. As to methods for preparing acid halides from the corresponding trialkylsilyl ester, U.S. Pat. No. 4,070,710 teaches the chlorination of a trimethylsilyl ester using thionyl chloride ($SOCl_2$). However, the anhydrous methodology required for these types of reactions makes commercial scale synthesis an oftentimes uneconomical.

SUMMARY OF THE INVENTION

The present invention provides a method for converting the ammonium salt of various carboxylic acids to the corresponding trialkylsilyl ester, while utilizing a silylation catalyst, preferably a tetra-alkyl ammonium halide. The resulting trialkylsilyl ester is then reacted in situ with a halogenating agent such as phosgene, to provide the acid chloride in excellent yield.

Preferred silylating agents are the silylated amines such as hexamethyldisilazane, while the preferred silylation catalyst is a tetra-alkylammonium halide, especially tetra-n-butylammonium bromide.

When the process is carried out under the preferred conditions, all by-products of the reaction are volatile, and thus, the acid halide formed may be used directly in a subsequent reaction without isolation. As such, the invention provides a process for preparing acid halides from the corresponding ammonium salt which is feasible on an industrial scale.

DETAILED DESCRIPTION OF THE INVENTION

The present invention provides a process for preparing trialkylsilyl esters of the formula

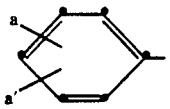

which comprises reacting a compound of the formula

with a trialkylsilylating reagent in an inert solvent in the presence of a silylation catalyst.

In the above formulae, R is the residue of any carboxylic acid. Preferably, R is the residue of a carboxylic acid side chain (RC(O)—) typically found at the 7-position of cephalosporins and/or the 6-position of penicillins. R', R" and R'" are individually $C_1-C_6$ alkyl groups.

As an especially preferred embodiment, R is hydrogen; $C_1-C_6$ alkyl, $C_1-C_6$ alkyl substituted by cyano, carboxy, halogen, amino, $C_1-C_4$ alkoxy, $C_1-C_4$ alkylthio, or trifluoromethylthio:

a phenyl or substituted phenyl group represented by the formula

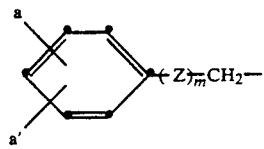

wherein a and a' independently are hydrogen, halogen, hydroxy, $C_1-C_4$ alkoxy, $C_1-C_4$ alkanoyloxy, $C_1-C_4$ alkyl, $C_1-C_4$ alkylthio, amino, $C_1-C_4$ alkanoylamino, $C_1-C_4$ alkylsulfonylamino, carboxy, carbamoyl, aminosulfonyl, hydroxymethyl, aminomethyl, or carboxymethyl;

a group represented by the formula

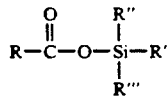

wherein a and a' have the same meanings as defined above, Z is O or S, and m is 0 or 1; - a heteroarylmethyl group represented by the formula

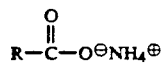

wherein $R^1$ is thienyl, furyl, benzothienyl, benzofuryl, pyridyl, 4-pyridylthio pyrimidyl, pyridazinyl, indolyl, pyrazolyl, imidazolyl, triazolyl, tetrazolyl, oxazolyl, thiazolyl, oxadiazolyl, thiadiazolyl, and such heteroaryl groups substituted by amino, hydroxy, halogen, $C_1-C_4$ alkyl, $C_1-C_4$ alkoxy, $C_1-C_4$ alkylsulfonylamino;

a substituted methyl group represented by the formula

wherein $R^2$ is cyclohex-1,4-dienyl, or a phenyl group or substituted phenyl group represented by the formula

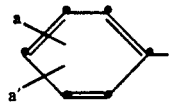

wherein a and a' have the above defined meanings, or $R^2$ is $R^1$ as defined above, and Q is hydroxy, $C_1-C_4$ alkanoyloxy, carboxy, sulfo, amino, sulfoamino amino or a substituted amino group represented by the formula

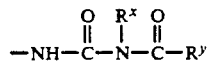

wherein $R^x$ is hydrogen or $C_1-C_3$ alkyl, $R^y$ is $C_1-C_4$ alkyl, furyl, thienyl, phenyl, halophenyl, nitrophenyl, styryl, halostyryl, nitrostyryl or a group

wherein $R^x$ is hydrogen or $C_1$-$C_3$ alkyl, and $R^z$ is hydrogen, $C_1$-$C_3$ alkylsulfonyl, $C_1$-$C_3$ alkyl, or $C_1$-$C_4$ alkanoyl; or Q is a substituted amino group represented by the formula

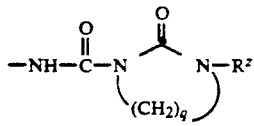

wherein $R^z$ has the same meanings as defined above and q is 2 or 3; or Q is a substituted amino group represented by the formula

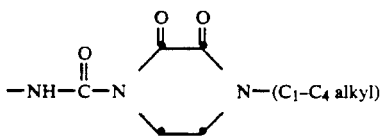

a benzamido group represented by the formula

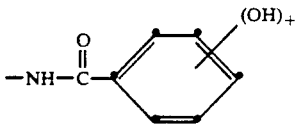

wherein t is 1 to 3;
a pyridone or hydroxy-substituted pyridone group represented by the formula

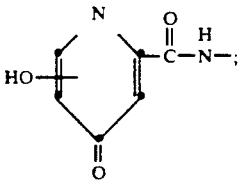

a pyridyl group represented by the formula

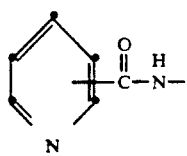

and such pyridyl group substituted by $C_1$-$C_4$ alkyl, amino, carboxy, hydroxy or halogen; an imidazoyl or pyrazolyl group represented by the formulae

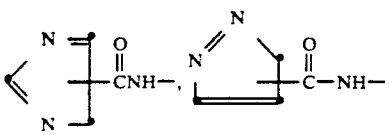

and such groups substituted by $C_1$-$C_4$ alkyl, carboxy, amino or halogen;

a benzpyridazin-4-one-3-ylcarbonylamino group represented by the formulae

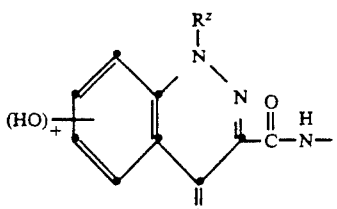

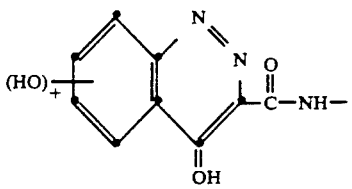

wherein $R^z$ is hydrogen or $C_1$-$C_4$ alkyl; and t is 1-3; or Q is a substituted amino group represented by the formula

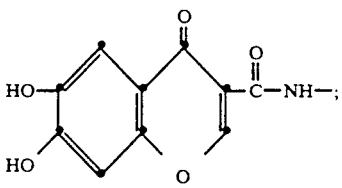

or R is a keto group or an oximino-substituted group represented by the formulae

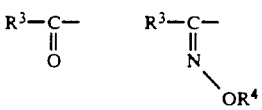

wherein $R^3$ is $R^1$ or $R^2$ as defined above and $R^4$ is hydrogen, $C_1$-$C_4$ alkyl, $C_1$-$C_4$ alkyl substituted by halogen, a carboxy-substituted alkyl or cycloalkyl group represented by the formula

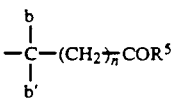

wherein b and b' independently are hydrogen, or $C_1$-$C_3$ alkyl, n is 0, 1, 2, or 3; and b and b' when taken together with the carbon to which they are bonded form a 3- to 6-membered carbocyclic ring, and $R^5$ is hydroxy, $C_1$-$C_4$ alkoxy, amino, $C_1$-$C_4$ alkylamino, or di($C_1$-$C_4$ alkyl)amino;

or $R^4$ is a cyclic lactam represented by the formula

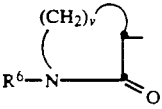

wherein v is 2, 3, or 4; and $R^6$ is hydrogen or $C_1$-$C_3$ alkyl;

or $R^4$ is a heteroarylmethyl group represented by the formula $$R^1-CH_2-$$

wherein R' has the same meanings as defined above.

In the above definition, $C_1-C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; $C_1-C_6$ alkyl substituted by cyano refers to cyanomethyl, cyanoethyl, 4-cyanobutyl, and the like; $C_1-C_6$ alkyl substituted by carboxy refers to such groups as carboxymethyl, 2-carboxyethyl, 2-carboxypropyl, 4-carboxybutyl, 5-carboxypentyl, and the like; $C_1-C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1-C_6$ alkyl substituted by amino refers to such groups as 2-aminoethyl, aminomethyl, 3-aminopropyl and 4-aminobutyl; $C_1-C_6$ alkyl substituted by $C_1-C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like groups; $C_1-C_6$ alkyl substituted by $C_1-C_4$-alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1-C_6$ alkyl substituted by trifluoromethyl is exemplified 2,2,2-trifluoroethyl, 3,3,3-trifluoropropyl, 4,4,4-trifluorobutyl, and the like; and $C_1-C_6$ alkyl substituted by trifluoromethylthio refers to, for example, trifluoromethylthiomethyl, 2-(trifluoromethylthio)ethyl, 2-(trifluoromethylthio)propyl, 4-(trifluoromethylthio)butyl, 5-(trifluoromethylthio)hexyl, and like $C_1-C_6$ alkyl substituted groups.

When in the above formulae R is a substituted phenyl group wherein the substituent(s) are represented by a and a', examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylaminophenyl such a 3-methylsulfonylaminophenyl, 4-methylsulfonylaminophenyl, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCO— groups of the above formulae wherein R is a group represented by the formula

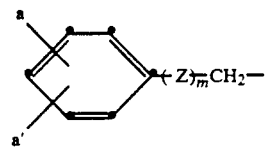

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=0, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R^1$—$CH_2CO$—groups wherein $R^1$ is a heteroaryl group are: 2-thienylacetyl, 3-thienylacetyl, -furylacetyl, 2-benzothienylacetyl, 2-benzofurylacetyl, -benzothienylacetyl, indol-2-ylacetyl, 1H-tetrazol-1-ylacetyl, oxazol-2-ylacetyl, oxazol-4-ylacetyl, thiazol4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, pyridyl-2-acetyl, pyridyl-3-acetyl, pyridyl-4-acetyl, 4-aminopyridyl-3-acetyl, pyrimidin-2-ylacetyl, pyrimidin-4-ylacetyl, 2-aminopyrimidin-4-ylacetyl, 4-aminopyrimidin-2-ylacetyl, pyridazin-3-acetyl, pyridazin-4-acetyl, pyrazol-3-ylacetyl, 3-methylpyrazol-1-ylacetyl, imidazol-2-ylacetyl, imidazol-1-ylacetyl, 2-aminoimidazol-3-ylacetyl, 3-chloroimidazol-4-ylacetyl, and like heteroaryl groups optionally substituted by amino, $C_1-C_4$ alkylsulfonylamino, hydroxy, halo, $C_1-C_4$ alkyl or $C_1-C_4$-alkoxy groups.

Examples of RCO- groups are compounds wherein R is a substituted methyl group represented by the formula $R^2$—CH(Q)— and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl, 2-formyloxy-2- phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-sulfoamino-2-phenylacetyl, 2-sulfoamino-2-(4-hydroxyphenyl)acetyl, 2-sulfoamino-2-(2-aminothiazol-4-yl)acetyl, 2-amino-2-(benzothien-2-yl)acetyl, 2-amino-2-(3-methylsulfonylphenyl)acetyl, 2-sulfoamino-2-(1,4-cyclohexadien)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl; and when Q is a substituted amino group represented by the formula

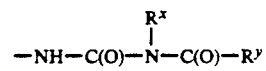

examples of such acyl groups are 2-(N-methyl-N-benzoylcarbamoylamino)-2-phenylacetyl, 2-(N-methyl-N-cinnamoylcarbamoylamino)-2-(2-furyl)acetyl, 2-(N,N-dimethylcarbamoylureido-2-(4-chlorophenyl)acetyl, 2-[N-methyl-N-(2-chlorocinnamoyl)carbamoylamino]-2-(2-thienyl)acetyl, and 2-(N-ethyl-N-acetylcarbamoylamino)2-(4-hydroxyphenyl)acetyl; and when Q is a substituted amino group represented by the formula

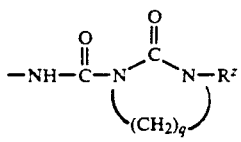

examples of acyl group R(CO—) are 2-[(3-methylimidazolidin-2-one-1-yl)carbonylamino]-2-phenylacetyl, 2-[(3-acetylimidazolidin-2-one-1yl)carbonylamino]-2phenylacetyl, 2-[(3-methylsulfonylimidazolidin-2-one-1-yl)-2-(2-thienyl)acetyl, and 2-[(3-acetylhexahydropyrimidin-2-one-1-yl)carbonylamino]-2-phenylacetyl; and when Q is a hydroxy-substituted benzamido group represented by the formula

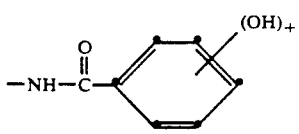

examples of such acyl groups are 2-(2,4-dihydroxybenzamido)-2-phenylacetyl, 2-(4-hydroxybenzamido)-2-(4-hydroxyphenyl)acetyl, 2-(3,4-dihydroxybenzamido)-2-(2-aminothiazol-4-yl)acetyl, 2-(3,5-dihydroxybenzamido)-2-(3-thienyl)acetyl, and 2-(2-hydroxybenzamido)-2-(2-benzofuryl)acetyl.

When Q is an hydroxy-substituted pyridinecarbonylamino group, examples include e.g., 2-hydroxypyridin-4-one-6-ylcarbonylamino and 3-hydroxypyridin-4-one-6-ylcarbonylamino. When Q is a pyridylcarbonylamino group examples are e.g., pyridin-3-ylcarbonylamino, 4-aminopyridin-3-ylcarbonylamino, 5-chloropyridin-2-ylcarbonylamino, 3-carboxypyridin-4-ylcarbonylamino, and 4-aminopyridino-2-ylcarbonylamino. When Q is an imidazole or pyrazole group as defined above examples include e.g., 2-aminoimidazol-4-ylcarbonylamino, 5-carboxy-2-methylimidazol-4-ylcarbonylamino, 5-carboxypyrazol-3-ylcarbonylamino, 3-aminopyrazol-4-ylcarbonylamino and 4-hydroxypyrazol-5-ylcarbonylamino. When Q is a benzpyridazin-4-one-3-ylcarbonylamino group, examples of Q are represented by the formulae (including the tautomeric form when $R^3 = H$)

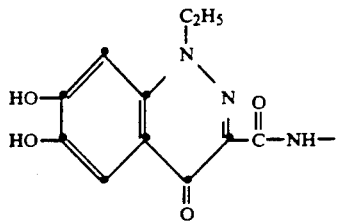

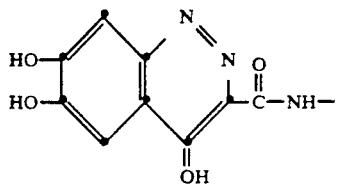

Examples of RCO acyl groups of the compounds represented by the above formulae when R is a keto group or an oximino-substituted group represented by the formulae

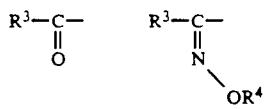

are the keto groups 2-oxo-2-phenylacetyl, 2-oxo-2-(2-thienyl)acetyl, 2-oxo-2-(2-aminothiazol-4-yl)acetyl: and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoylprop-2-yl)oxyiminoacetyl, 2-(5-amino-1,3,4-thiadiazol-2-yl)-2-methoxyiminoacetyl, 2-(2-aminothiazol-4-yl)-2-(pyrrolidin-2-one-yl)oxyiminoacetyl, 2-(2-aminothiazol-4-yl)-2-(1-methylpyrrolidin-2-one-3-yl)oxyiminoacetyl, 2-phenyl-2-(pyrrolidin-2-one-3-yl)oxyiminoacetyl, 2-(2-aminooxazol-4-yl)-2-(1-ethylpyrrolidin-2-one-3-yl)oxyiminoacetyl, 2-(2-aminothiazol-4-yl)-2-(1-ethylpiperidin-2-one-3-yl)-2-oxyiminoacetyl, and 2-(2-furyl)-2-(pyrrolidin-2-one-3-yl)oxyiminoacetyl.

A further preferred group is represented by the above formulae wherein R is the group

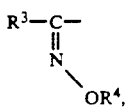

in the syn form.

Particularly preferred compounds are represented when $R^4$ is $C_1$–$C_4$ alkyl or a carboxy substituted alkyl group such as carboxymethyl, 2-carboxyethyl, 3-carboxypropyl, 2-carboxy-2-propyl or a $C_1$–$C_4$ alkyl substituted with amino such as 2-aminoethyl; and $R^3$ is a five or six membered heterocyclic ring $R^1$, in particular, an amino substituted heterocyclic. Especially preferred heterocyclics are the 2-aminothiazole or 2-aminooxazole ring.

The most highly preferred group is when R is a group of the formula

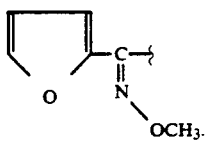

As one skilled in the art will appreciate, whenever a functional group such as an amino, a hydroxy, a mercapto, or a second or further subsequent carboxy group is present in the R group, it (they) will be by necessity be protected using conventional techniques appropriate to the formation of the desired acid halide. As used herein, the term "halide" in "acid halide" refers to chloro, bromo, and fluoro.

Further, as used herein, the term "suitable trialkylsilylating reagent" encompasses compounds of the general formulae

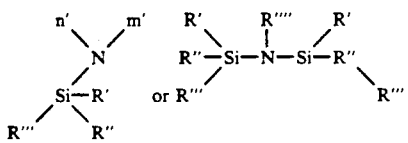

wherein R', R'', and R''' are individually $C_1$–$C_6$ alkyl groups, n', m' and R'''' are individually hydrogen or $C_1$–$C_3$ alkyl groups.

The following trialkylsilylating reagents are examples of such compounds deemed efficacious in the process of the present invention: dimethylaminotrimethylsilane, methylaminotrimethylsilane, diethylaminotrimethylsilane, aminotrimethylsilane and hexamethyldisilazane (HMDS). HMDS is the preferred trialkylsilylating reagent.

Preferred silylation catalysts in the above reaction are of the general formula ($C_1$–$C_6$ alkyl)-+NBr−, with tetra-n-butylammonium bromide being the most highly preferred catalyst.

A further class of suitable silylating catalysts are those described in U.S. Pat. No. 4,400,509, incorporated herein by reference. In general, this class of compounds is represented by the formula X'-NH-Y, wherein X' and Y are individually an electron-withdrawing group or when X is an electron-withdrawing group, Y is selected from the group consisting of hydrogen and trialkylsilyl of 1 to 6 carbon atoms or X and Y together with the nitrogen atom to which they are attached form a cyclic electron-withdrawing group. Specific preferred examples of this type of silylation catalyst include trichloroacetamide, trifluoroacetamide, phthalimide, 3,4,5,6-tetrachlorophthalimide, 3,4,5,6-tetrabromophthalimide, 1,8-naphthalimide, maleimide, barbituric acid, saccharine, N-benzoyl-4-toluenesulfonamide, N-(2-methoxybenzoyl)-4-toluenesulfonamide, N-(1-naphthoyl)-4-toluenesulfonamide, N-benzoylbenzenesulfonamide, N-(2-methoxy-1-naphthoyl)-4-toluenesulfonamide, N-(2-methoxy-1-naphthoyl)-methanesulfonamide, di-(4-toluenesulfonyl)-amine, dimethyl N-(trichloroacetyl)-phosphoramidates, di-4-nitrophenyl N-(trichloroacetyl)-phosphoramidate, di-4-nitrophenyl N-(p-toluenesulfonyl)-phosphoramidate, diisopropyl N-(dichloroacetyl)-phosphoramidate, di-o-chlorophenyl N-(4-chlorophenylsulfonyl)-phosphoramidate, tetraphenyl imidodiphosphate, sulfamide, N,N-dimethylsulfamide, N,N'-bis-(trimethylsilyl)sulfamide, 1,2-benzisothiazol-3-(2H)-one and 4-benzoyloxy-1,2-dihydro-1-oxo-phthalazine. Finally, a further suitable silylation catalyst in the above reaction is 4-dimethylaminopyridine.

Suitable inert solvents which can be used in the present invention include aprotic solvents such as dichloromethane, dichloroethane, dichloroethylene, dioxane, tetrahydrofuran, acetonitrile, toluene, chlorobenzene, hexane, and the like. Dichloromethane is the preferred inert solvent. The choice of perhaps other suitable solvents is well within the knowledge of one skilled in the art, and, of course, the above listing is by no means exhaustive.

In carrying out the process, the ammonium salt

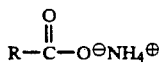

is first slurried in an inert solvent such as dichloromethane. Next, a suitable trialkylsilylating reagent such as HMDS is added in 60–90 mole % along with a silylation catalyst such as tetra n-butylammonium bromide. The reaction mixture is then preferably heated to the reflux temperature of the chosen solvent in order to remove volatile reaction by-products, and stirring is continued until the reaction is substantially complete. In the case wherein R is

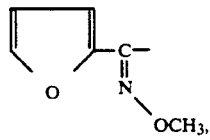

the completion of the reaction will be evidenced by the disappearance of the relatively insoluble ammonium salt slurry.

As noted above, the preferred aspect of the present invention is when the chosen trialkylsilylating reagent and catalyst form volatile by-products which can be removed by heating from a temperature of about 25° C to 60° C, preferably to the reflux temperature of the chosen solvent. However, one skilled in the art will recognize that the transformation from the ammonium salt of a carboxylic acid to the corresponding trialkylsilyl ester may be accomplished using trialkylsilylating reagents and/or catalysts which are not volatile; thus, isolation of the trialkylsilyl ester or ensuing acid halide may be necessary before further derivatization. Further, the choice of solvent will, of course, also dictate the reflux temperature of the reaction mixture, and such choice is well within the skill of one of ordinary skill in the art. Alternatively, the volatile by-products may be removed by reduced pressure or by purging with an inert gas such as $N_2$.

As a further aspect of the present invention, there are provided novel intermediates of the formula

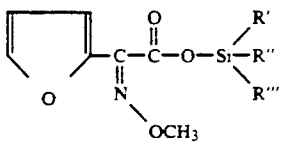

wherein R', R", and R'" are individually $C_1$-$C_6$ alkyl. The intermediates of the above formula wherein R', R", and R'" are methyl are especially preferred.

As yet a further aspect of the present invention, there is provided a two-step process for preparing acid chlorides which comprises a) trialkylsilylating a compound of the formula

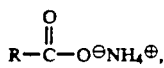

with a suitable trialkylsilylating reagent in an inert solvent in the presence of a silylation catalyst, followed by b) chlorination with phosgene.

As used herein, the terms R, suitable trialkylsilylating reagent, inert solvent, and silylation are as described previously.

It is important to note that one further attribute of the processes of the present invention is that the integrity of the oxime function is left substantially undisturbed; i.e., formation of the acid halide results in little, if any, detectable regioisomerization of the oxime from the syn to anti configuration.

As illustrated below in Example 1, one principal utility for the carboxylic acid halides produced by the present invention is in the acylation of the 6-amino moiety of penicillins and the 7-amino moiety of cephalosporins (and 1-carba(1-dethia)cephalosporins.

The following examples are set forth to further illustrate the present invention but are in no manner to be construed as limiting the scope thereof.

EXAMPLE 1

(Z)-7-[[2-furyl(methoximino)acetyl]amino] cephalosporanic acid

2-Furyl-methoxime acetic acid ammonium salt syn isomer (19.2 g, 103 mmol), tetrabutylammonium bromide (0.6 g), and hexamethyldisilazane (15.3 ml) were refluxed in 189 ml of methylene chloride for 3 hrs. HPLC analysis indicated at least a 92% conversion to 2-furyl-methoxime acetic acid trimethylsilyl ester. To two-thirds of the above methylene chloride solution (137 ml, 62.3 mmol) was added dimethylacetamide (19.8 ml). The solution was cooled to $-10°$ C. and phosgene (5.8 ml) was added slow enough to maintain the temperature at $-5°$ to $-10°$ C. The reaction mixture was stirred for 1 hr at $-10°$ C. Derivatization of a sample of the 2-furyl-methoximino acetyl chloride as the amide indicated a 92.8% overall yield of acid chloride by HPLC. A slurry of 7-aminocephalosporanic acid (8.33 g, 29.0 mmol) in methylene chloride at $-10°$ C. was dissolved by the addition of triethylamine (7 ml). This solution was added to a solution of the above acid chloride (77 ml, 31.9 mmol) at $-10°$ C. to maintain the temperature at less than $-5°$ C. The mixture was stirred 1 hr at which time HPLC analysis indicated an 82% yield of the title compound in solution was obtained. The mixture was concentrated by vacuum distillation to 30 to 40 ml and deionized water (70 ml) was added. The pH of the mixture was adjusted to 5.2 with 5-N sodium hydroxide solution and the remaining methylene chloride was removed by vacuum distillation. The product was precipitated by adjusting the pH to 2.0 with 5 N hydrochloric acid. The slurry was stirred for 20° C. for 15 min and then at 0° to 5° C. for 1 hr. The solids were collected by filtration and reslurried in water (50 ml) at 0° to 5° C. The product was vacuum dried at 35° C. overnight to give 9.71 g (66% potency, 15.1 mmol) of the title compound, (Z)-7-[[2-furyl(methoximino)acetyl-]amino]cephalosporanic acid. $^1$H-NMR (80 MHz, $d_6$-DMSO) ppm 9.81 (1H, d, J=7.8 Hz), 7.88 (1H, br. s), 6.74 (2H, m), 5.86 (1h, dd, J=7.8, 4.9 Hz), 5.24 (1H, d, J=4.9 Hz), 5.06 (1H, AB, J=12.9 Hz), 4.77 (1H, AB, J=12.9 Hz), 3.95 (3H, s), 3.64 (2H, m), 2.09 (3H, s).

EXAMPLE 2

Trimethylsilyl phenoxyacetate

Phenoxyacetic acid ammonium salt, tetrabutylammonium bromide, and hexamethyldisilazane are refluxed in methylene chloride to provide the title compound.

EXAMPLE 3

Trimethylsilyl 2-(2-tritylaminothiazol-4-yl)-2-methoxyiminoacetate 2-(2-Tritylaminothiazol-4-yl)-2-methoximino acetic acid ammonium salt, tetrabutylammonium bromide, and hexamethyldisilazane are refluxed in methylene chloride to provide the title compound.

I claim:

1. A compound of the formula

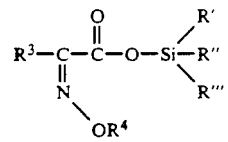

wherein $R^4$ is hydrogen, $C_1$-$C_4$ alkyl, $C_1$-$C_4$ alkyl substituted by halogen, a carboxy-substituted alkyl or cycloalkyl group represented by the formula

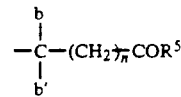

wherein b and b' independently are hydrogen, or $C_1$-$C_3$ alkyl, n is 0, 1, 2, or 3; and b and b' when taken together with the carbon to which they are bonded form a 3- to 6-membered carbocyclic ring, and $R^5$ is hydroxy, $C_1$-$C_4$ alkoxy, amino, $C_1$-$C_4$ alkylamino, or di($C_1$-$C_4$ alkyl)amino; or $R^4$ is a cyclic lactam represented by the formula

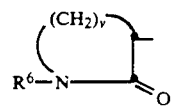

wherein v is 2, 3, or 4; and $R^6$ is hydrogen or $C_1$-$C_3$ alkyl;

R', R" and R'" are individually $C_1$-$C_6$ alkyl groups; and $R^3$ is thienyl, furyl, benzothienyl, benzofuryl, pyridyl, 4-pyridylthio pyrimidyl, pyridazinyl, indolyl, pyrazolyl, imidazolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, $C_1$-$C_4$ alkylsulfonylamino; or cyclohex-1,4-dienyl, a phenyl group or substituted phenyl group represented by the formula

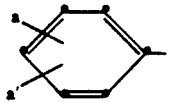

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, aminosulfonyl, hydroxymethyl, aminomethyl, or carboxymethyl.

2. A compound of the formula

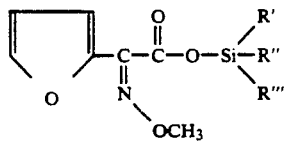

wherein R', R", and R'" are individually $C_1$-$C_6$ alkyl.

3. A compound according to claim 2, wherein R', R", and R'" are each methyl.

* * * * *